(12) United States Patent
Alani et al.

(10) Patent No.: US 11,752,096 B2
(45) Date of Patent: Sep. 12, 2023

(54) TARGETED DELIVERY OF ANTI-CSF1R ANTIBODIES TO JOINTS WITH TENOSYNOVIAL GIANT CELL TUMORS

(71) Applicant: AmMax Bio, Inc., Redwood City, CA (US)

(72) Inventors: Laman Alani, Menlo Park, CA (US); Kirk William Johnson, Moraga, CA (US); Michael Huang, Redwood City, CA (US); Chung-Chiang Hsu, Los Altos Hills, CA (US)

(73) Assignee: AmMax Bio, Inc., Redwood City, CA (US)

( * ) Notice: Subject to any disclaimer, the term of this patent is extended or adjusted under 35 U.S.C. 154(b) by 0 days.

(21) Appl. No.: 17/821,459

(22) Filed: Aug. 22, 2022

(65) Prior Publication Data

US 2023/0065193 A1 Mar. 2, 2023

Related U.S. Application Data

(63) Continuation of application No. PCT/US2022/074928, filed on Aug. 12, 2022.

(60) Provisional application No. 63/232,611, filed on Aug. 12, 2021.

(51) Int. Cl.
*A61K 9/00* (2006.01)
*C07K 16/28* (2006.01)
*A61P 35/00* (2006.01)
*A61P 19/02* (2006.01)
*A61K 39/00* (2006.01)

(52) U.S. Cl.
CPC ............ *A61K 9/0019* (2013.01); *A61P 19/02* (2018.01); *A61P 35/00* (2018.01); *C07K 16/2866* (2013.01); *A61K 2039/505* (2013.01); *A61K 2039/54* (2013.01); *A61K 2039/545* (2013.01)

(58) Field of Classification Search
CPC .............................. A61P 19/02; A61K 9/0019
See application file for complete search history.

(56) References Cited

U.S. PATENT DOCUMENTS

| 8,529,897 B2 | 9/2013 | Washburn et al. |
| 2014/0328764 A1 | 11/2014 | Tang et al. |
| 2017/0002060 A1* | 1/2017 | Bolen .................... C07K 16/00 |

FOREIGN PATENT DOCUMENTS

| WO | WO 2017175200 A1 | 10/2017 | |
| WO | WO2020232051 | * 11/2020 | ............. C07K 16/30 |

OTHER PUBLICATIONS

Benner et al.—Drug Design, Development and Therapy, 14, 1693-1704, 2020. (Year: 2020).*
Mach et al. "Electrostatic interactions of monoclonal antibodies with subcutaneous tissue" Ther Deliv, Jun. 2011, vol. 2, No. 6, pp. 1-10, especially, Abstract; p. 5, col. 1, para 1; p. 6, col. 1, para 6; col. 2, para 2; Fig. 5; Fig, o/; Fig. 8; Fig. 7 legend, (11 pages).
Tian et al. "Hyaluronic acid hydrogel as Nogo-66 receptor antibody delivery system for the repairing of injured rat brain: in vitro" Journal of Controlled Release. 2005, vol. 102, No. 1, pp. 13-22, whole document, (10 pages).

\* cited by examiner

*Primary Examiner* — Elly-Gerald Stoica
(74) *Attorney, Agent, or Firm* — Sheppard Mullin Richter & Hampton LLP

(57) ABSTRACT

The present disclosure provides compositions and methods for intra-articular delivery of anti-CSF1R antibodies to a tissue that is impacted by a disease that is treatable with CSF1/CSF1R inhibition and/or that expresses CSF1R. It was conventional knowledge that the intra-articular dwell time of proteins in joints is typically a few hours or less. The present disclosure shows, however, that intra-articular delivery of an anti-CSF1R antibody can lead to sustained exposure and pharmacologic activity of the antibody in the joints far beyond a few hours, providing an effective means for targeted and extended delivery of the therapeutic agent.

18 Claims, 2 Drawing Sheets

Specification includes a Sequence Listing.

SEQUENCE LISTING

```
Sequence total quantity: 10
SEQ ID NO: 1                   moltype = AA    length = 446
FEATURE                        Location/Qualifiers
source                         1..446
                               mol_type = protein
                               organism = synthetic construct
SEQUENCE: 1
QVQLVQSGAE VKKPGASVKV SCKASGYTFT SYDISWVRQA PGQGLEWMGV IWTDGGTNYA   60
QKLQGRVTMT TDTSTSTAYM ELRSLRSDDT AVYYCARDQR LYFDVWGQGT TVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 2                   moltype = AA    length = 213
FEATURE                        Location/Qualifiers
source                         1..213
                               mol_type = protein
                               organism = synthetic construct
SEQUENCE: 2
DIQMTQSPSS LSASVGDRVT ITCRASEDVN TYVSWYQQKP GKAPKLLIYA ASNRYTGVPS   60
RFSGSGSGTD FTLTISSLQP EDFATYYCQQ SFSYPTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 3                   moltype = AA    length = 449
FEATURE                        Location/Qualifiers
source                         1..449
                               mol_type = protein
                               organism = synthetic construct
SEQUENCE: 3
QVQLVQSGAE VKKPGSSVKV SCKASGYTFT DNYMIWVRQA PGQGLEWMGD INPYNGGTTF   60
NQKFKGRVTI TADKSTSTAY MELSSLRSED TAVYYCARES PYFSNLYVMD YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 4                   moltype = AA    length = 218
FEATURE                        Location/Qualifiers
source                         1..218
                               mol_type = protein
                               organism = synthetic construct
SEQUENCE: 4
EIVLTQSPAT LSLSPGERAT LSCKASQSVD YDGDNYMNWY QQKPGQAPRL LIYAASNLES   60
GIPARFSGSG SGTDFTLTIS SLEPEDFAVY YCHLSNEDLS TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 5                   moltype = AA    length = 450
FEATURE                        Location/Qualifiers
source                         1..450
                               mol_type = protein
                               organism = synthetic construct
SEQUENCE: 5
QDQLVESGGG VVQPGRSLRL SCAASGFTFS SYGMHWVRQA PGEGLEWVAV IWYDGSNKYY   60
ADSVKGRFTI SRDNSKNTLY LQMNSLRAED TAVYYCARGD YEVDYGMDVW GQGTTVTVAS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 6                   moltype = AA    length = 214
FEATURE                        Location/Qualifiers
source                         1..214
                               mol_type = protein
                               organism = synthetic construct
SEQUENCE: 6
AIQLTQSPSS LSASVGDRVT ITCRASQGIS NALAWYQQKP GKAPKLLIYD ASSLESGVPS   60
RFSGSGSGTD FTLTISSLQP EDFATYYCQQ FNSYPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 7              moltype = AA  length = 446
FEATURE                   Location/Qualifiers
source                    1..446
                          mol_type = protein
                          organism = synthetic construct
SEQUENCE: 7
QVQLVQSGAE VKKPGASVKV SCKASGYTFT SYGISWVRQA PGQGLEWMGW ISAYNGNTNY   60
AQKLQGRVTM TTDTSTSTAY MELRSLRSDD TAVYYCARES WFGEVFFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                      446

SEQ ID NO: 8              moltype = AA  length = 220
FEATURE                   Location/Qualifiers
source                    1..220
                          mol_type = protein
                          organism = synthetic construct
SEQUENCE: 8
DIVMTQSPDS LAVSLGERAT INCKSSQSVL DSSDNKNYLA WYQQKPGQPP KLLIYWASNR   60
ESGVPDRFSG SGSGTDFTLT ISSLQAEDVA VYYCQQYYSD PFTFGPGTKV DIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 9              moltype = AA  length = 453
FEATURE                   Location/Qualifiers
source                    1..453
                          mol_type = protein
                          organism = synthetic construct
SEQUENCE: 9
EVTLKESGPA LVKPTQTLTL TCTFSGFSLT TYGMGVGWIR QPPGKALEWL ANIWWDDDKY   60
YNPSLKNRLT ISKDTSKNQV VLTMTNMDPV DTATYYCARI GPIKYPTAPY RYFDFWGQGT  120
MVTVSSASTK GPSVFPLAPC SRSTSESTAA LGCLVKDYFP EPVTVSWNSG ALTSGVHTFP  180
AVLQSSGLYS LSSVVTVPSS SLGTKTYTCN VDHKPSNTKV DKRVESKYGP PCPPCPAPEF  240
LGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LGK                              453

SEQ ID NO: 10             moltype = AA  length = 214
FEATURE                   Location/Qualifiers
source                    1..214
                          mol_type = protein
                          organism = synthetic construct
SEQUENCE: 10
DIQMTQSPSS LSASVGDRVT ITCLASEDIY DNLAWYQQKP GKAPKLLIYY ASSLQDGVPS   60
RFSGSGSGTD YTLTISSLQP EDFATYYCLQ DSEYPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

TARGETED DELIVERY OF ANTI-CSF1R ANTIBODIES TO JOINTS WITH TENOSYNOVIAL GIANT CELL TUMORS

CROSS REFERENCE TO RELATED APPLICATIONS

This application is a continuation of International Patent Application No. PCT/US2022/074928, filed Aug. 12, 2022, which claims the benefit under 35 U.S.C. § 119(e) of the U.S. Provisional Application Ser. No. 63/232,611, filed Aug. 12, 2021, the content of each of which is hereby incorporated by reference in its entirety.

REFERENCE TO AN ELECTRONIC SEQUENCE LISTING

The contents of the electronic sequence listing (72GZ_332298_US.xml; Size: 12,898 bytes; and Date of Creation: Aug. 10, 2022) is herein incorporated by reference in its entirety.

BACKGROUND

Tenosynovial giant cell tumor (TGCT) is a neoplasm derived from the synovium that causes recruitment of immune cells, specifically macrophages, leading to formation of a mass. TGCT is a localized disease and can also diffuse to nearby tissues. The tumors are often classified by their growth pattern (localized or diffuse) and site (intra- or extra-articular).

Localized TGCT is characterized by a discrete nodule. While any location is possible, localized forms mainly involve the digits joints and wrist (85% of cases); foot and ankle, knee, hip or other joint locations are more rare. Diffuse forms mainly involve the large joints: knee, hip, ankle and elbow. Localized forms are systematically benign; diffuse forms are more aggressive and destructive, and may exceptionally include a malignant component.

Current treatment options for TGCT are limited, including surgery and radiotherapy. Surgery is often the treatment of choice for patients with TGCT. Localized TGCT is managed by marginal excision. Recurrences occur in 8-20% of patients and are managed by re-excision. Diffuse TGCT tends to recur more often (33-50%) and has a much more aggressive clinical course. Patients are often symptomatic and require multiple surgical procedures during their lifetime. In some cases, the joint may need to be replaced. There is currently one FDA-approved systemic pharmacotherapy for the treatment of TGCT. Turalio (pexidartinib) was approved in the US for the treatment of TGCT associated with severe symptoms not amenable to surgery. While effective at reducing tumor size, Turalio is associated with a significant risk of hepatotoxicity and its use has been limited by a black box warning and REMS.

A potential therapy for TGCT targets a cytokine called colony stimulating factor 1 (CSF1) or its receptor, colony stimulating factor 1 receptor (CSF1R). CSF1R-mediated signaling is crucial for the differentiation and survival of the mononuclear phagocyte system. The CSF1-CSF1R axis is the predominant driver of TGCT development given the neoplasia typically over-expresses CSF1 which acts in an autocrine manner to expand the neoplastic cells and a paracrine manner to recruit other mononuclear phagocytes, giant cells, and osteoclasts adding to the tumor mass.

Several anti-CSF1 and anti-CSF1R antibodies are, or have been, in clinical development, for treating various solid tumors including TGCT. Examples include emactuzumab (anti-CSF1R, SynOx and Roche), cabiralizumab (anti-CSF1R, Five Prime and BMS), lacnotuzumab (anti-CSF1, Novartis and Xoma), PD-0360324 (anti-CSF1, Pfizer), axatilimab (anti-CSF1R, Syndax and UCB Biopharma), and IMC-CS4 (anti-CSF1R, Eli Lilly and ImClone).

SUMMARY

Figure 1:
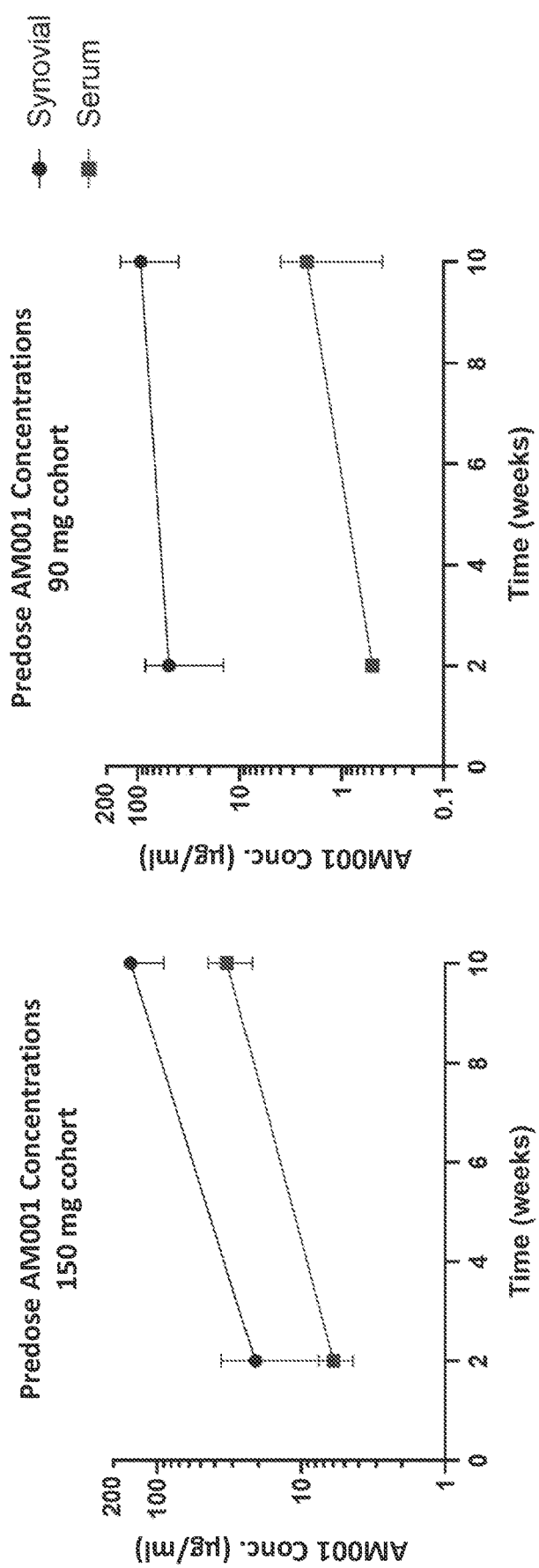
FIG. 1 shows that intra-articular administration of AM001 yielded high, sustained synovial concentrations with markedly reduced serum levels, in both patient cohorts (150 mg and 90 mg).

The present disclosure provides compositions and methods for intra-articular delivery of anti-CSF1R antibodies to a tissue that is impacted by a disease that is treatable with CSF1/CSF1R inhibition or that expresses CSF1R. It was conventional knowledge that the intra-articular dwell time of proteins in joints is typically a few hours or less. The present disclosure shows, however, that intra-articular delivery of an anti-CSF1R antibody can lead to sustained exposure of the antibody in the joints, providing an effective means for targeted and extended delivery of the therapeutic agent. Moreover, this property is shown in TGCT patients to exhibit pharmacologic activity weeks after a single administration and to reduce tumor burden and related symptoms in human TGCT patients as early as 6 weeks following initiation of a treatment regimen.

One embodiment of the present disclosure provides a method for administering an anti-CSF1R (colony stimulating factor 1 receptor) antibody to a mammalian subject, comprising local administration of a composition comprising the antibody at or proximate to a tissue in the mammalian subject, wherein the tissue comprises at least a cell that expresses CSF1R on the surface.

Also provided is a method for treating tenosynovial giant cell tumor (TGCT) in a patient, comprising administering an anti-CSF1R (colony stimulating factor 1 receptor) antibody at or proximate to the TGCT in the patient.

DETAILED DESCRIPTION

I. Definitions

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

The term "administration" refers to introducing an agent into a patient. An effective amount can be administered, which can be determined by the treating physician or the like. The related terms and phrases administering" and "administration of", when used in connection with a compound or tablet (and grammatical equivalents) refer both to direct administration, which may be administration to a patient by a medical professional or by self-administration by the patient.

"Therapeutically effective amount" or "effective amount" refers to an amount of a drug or an agent that when administered locally via a pharmaceutical composition described herein to a patient suffering from a condition, will have an intended therapeutic effect, e.g., alleviation, amelioration, palliation or elimination of one or more symptoms of the condition in the patient. The full therapeutic effect does not necessarily occur immediately and may occur only after a therapeutically effective amount is being delivered continuously for a period of time. For slow release or controlled release formulation, "therapeutically effective amount" or "effective amount" may refer to the total amount that is effective over a period of time, which is slowly released from the delivery vehicle to the disease site at an ascertainable and controllable release rate that constantly provides an effective amount of the drug to the disease site. In some embodiments, "therapeutically effective amount" or "effective amount" refers to an amount released to the disease site at a given period of time, e.g., per day.

The term "near," when referring to a tissue targeted for administration, means the intended target tissue and surrounding area. In some embodiments, the proximity is within 5 cm, 4 cm, 3 cm, 2 cm, 1.5 cm, 1 cm, 0.8 cm, 0.6 cm, 0.5 cm, 0.4 cm, 0.3 cm, 0.2 cm or 0.1 cm from the tissue.

The term "biodegradable," as used herein, means a polymer that dissolves or degrades within a period that is acceptable in the desired application, less than about five years and most preferably less than about one year, after exposure to a biological environment. For example, a polymer may be biodegradable in a physiological solution of pH 6-8 at a temperature of between about 25° C. and 38° C.

The term "pharmaceutically acceptable" refers to generally safe and non-toxic for human administration.

"Treatment", "treating", and "treat" are defined as acting upon a disease, disorder, or condition with an agent to reduce or ameliorate the harmful or any other undesired effects of the disease, disorder, or condition and/or its symptoms.

Unless otherwise specified, the terms "drug," "active ingredient," "active pharmaceutical ingredient," "therapeutic agent" and "API" are used synonymously to refer to the component in the composition that has a desired therapeutic effect.

"Antibody" means a human or non-human antibody, including humanized antibodies, and may be polyclonal or monoclonal, and/or chimeric antibodies. The term "antibody" includes antibody fragments capable of binding to antigen and may be selected from Fab, an Fv, an scFv, Fab' and Fab". The antibody may be of any isotype. The antibody can be wild-type or can include one or more mutations. For example, the mutation may be a conservative substitution of a cysteine residue. An "anti-CSF1R antibody" has the corresponding meaning with respect to an antibody to the CSF1R receptor.

Colony stimulating factor 1 (CSF-1), also known as macrophage colony stimulating factor (M-CSF), is a cytokine produced by a variety of cells, including macrophages, endothelial cells and fibroblasts. CSF-1 is composed of two "monomer" polypeptides, which form a biologically active dimeric CSF-1 protein. CSF-1 exists in at least three mature forms due to alternative RNA splicing (see, Cerretti et al. Molecular Immunology, 25:761 (1988)). The three forms of CSF-1 are translated from precursors, which encode polypeptide monomers of 256 to 554 amino acids, having a 32 amino acid signal sequence at the amino terminal and a putative transmembrane region of approximately 23 amino acids near the carboxyl terminal. The precursor peptides are subsequently processed by amino terminal and carboxyl terminal proteolytic cleavages to release mature CSF-1. Residues 1-149 of all three mature forms of CSF-1 are identical and are believed to contain sequences essential for biological activity of CSF-1. CSF-1 monomers are dimerized in vivo via disulfide-linkage and are glycosylated. CSF-1 belongs to a group of biological agonists that promote the production of blood cells. Specifically, it acts as a growth and differentiation factor for bone marrow progenitor cells of the mononuclear phagocyte lineage.

Colony stimulating factor 1 receptor (referred to herein as CSF1R; also referred to as FMS, FIM2, C-FMS, or CD115) is a single-pass transmembrane receptor with an N-terminal extracellular domain (ECD) and a C-terminal intracellular domain with tyrosine kinase activity. CSF1R belongs to the type III protein tyrosine kinase receptor family, and binding of CSF1 or the interleukin 34 ligand induces homodimerization of the receptor and subsequent activation of receptor signaling. CSF1R-mediated signaling is crucial for the differentiation and survival of the mononuclear phagocyte system and macrophages in particular.

"Thermogel" refers to a composition, which undergoes a phase transition from a liquid phase to gel phase when the temperature is raised above or reduced below a critical value, which is referred to as "transition temperature" or "gelation temperature." The term "liquid phase" or "liquid state" refers to a liquid or flowable form, such as a state having a viscosity of less than 2000 Pascal-seconds. The term "gel phase" or "gel state" refers to a gel or relatively solid form, such as a state having a viscosity of greater than 10,000 Pascal-seconds. In some embodiments, the phase transition from a liquid to a gel and vice versa occurs in less than 10 minutes, or in less than 5 minutes or in less than 2 minutes.

"Gel" refers to a semi-solid phase. For example, when the temperature of a thermogel is raised to or above the gelation temperature of the thermogel, the thermogel becomes a gel while it behave as liquid at temp below the gelation temperature.

"Aqueous solvent" refers to water or a water-based solution, e.g. an aqueous salt solution, such as a saline solution, phosphate buffered saline (PBS), and other aqueous solutions suitable for preparing an injectable pharmaceutical composition. An aqueous salt solution may contain one or more biocompatible salts selected from sodium chloride (NaCl), potassium chloride (KCl), sodium sulfate ($Na_2SO_4$), sodium bisulfate ($NaHSO_4$), sodium phosphate ($Na_3PO_4$), monosodium phosphate ($NaH_2PO_4$), disodium phosphate ($Na_2HPO_4$), potassium phosphate ($K_3PO_4$), monopotassium phosphate ($KH_2PO_4$), dipotassium phosphate ($K_2HPO_4$), various soluble calcium and magnesium salts, such as calcium chloride ($CaCl_2$), magnesium chloride ($MgCl_2$) and other salts formed by a combination of a cation selected from the group consisting of sodium, potassium, calcium, magnesium, ammonium, and tetraalkylammonium, with an anion selected from the group consisting of chloride, bromide, tartrate, mesylate, acetate, maleate, and oxalate and other biocompatible, water soluble salts including those

II. Targeted Delivery of Anti-CSF1R Antibodies

It was discovered in the present disclosure that, when the anti-CSF1R antibody AM001 was administered, intra-articularly, to the knees of TGCT patients, the antibody effectively shrank synovial TGCT. CSF1R inhibition has been tested for treating TGCT, via intravenous injections or oral administration (of a small molecule inhibitor). No local administration, however, has been tried or proposed.

Local administration, such as intra-articular injection, has significant clinical benefits. For instance, Evans et al. (*Nat Rev Rheumatol.* 2014 January; 10(1): 11-22) noted that "Diarthrodial joints are well suited to intra-articular injection, and the local delivery of therapeutics in this fashion brings several potential advantages to the treatment of a wide range of arthropathies. Possible benefits include increased bioavailability, reduced systemic exposure, fewer adverse events, and lower total drug costs." Abstract. Nevertheless, Evans further noted, "intra-articular therapy is challenging because of the rapid egress of injected materials from the joint space; this elimination is true of both small molecules, which exit via synovial capillaries, and of macromolecules, which are cleared by the lymphatic system." Id.

In particular, "Because lymphatic drainage is highly efficient, the intra-articular dwell time of proteins in joints is typically a few hours or less. This timescale presents obvious problems when attempting to treat chronic joint disorders with large molecules" (under subheading "Macromolecules have short dwell time"). A dwell time of just a few hours may be sufficient for treating conditions such as pain and inflammation, but is far from being useful for treating chronic diseases such as TGCT.

It is not surprising, therefore, that no intra-articular treatments have been tested or proposed for TGCT, prior to the present disclosure. In this context, it is therefore truly unexpected that, as demonstrated in the Examples, when AM001 was injected intra-articularly to TGCT patients, it resulted in Objective Responses (>30% tumor reduction by MRI) in 3/8 patients by long lesion dimension (RECIST1.1) and 4/8 patients by short lesion dimension (Modified RECSIST). Also important, the average synovial AM001 drug level at two weeks after just a single dose was still 17,237 ng/ml (with an average serum level at 5,962 ng/ml which further indicates sustained synovial or depot residence). Furthermore, synovial drug levels demonstrated accumulation with bi-weekly dosing thus further supporting extended residence. As shown in Example 4, intra-articular administration of AM001 yielded high, sustained synovial concentrations while in these patients the serum antibody levels were markedly reduced (FIG. 1). In addition, all patients exhibited trends for improved range of motion and reduced pain. Three patients received a 90 mg dose bi-weekly and pharmacokinetic, pharmacodynamic, and tumor reduction responses were similar (and dose-proportional) to the 150 mg cohort.

Without being bound by any particular theory, it is contemplated that intra-articularly delivered anti-CSF1R antibodies bind to the CSF1R protein expressed on the tumor cells, such as intratumoral CSF1R$^+$ macrophages. The high abundance of CSF1R expressed on the tumor cells allow the anti-CSF1R antibodies to be concentrated in the tumor area, reducing their clearance by lymphatic drainage.

In accordance with one embodiment of the disclosure, therefore, provided is a method for administering an anti-CSF1R (colony stimulating factor 1 receptor) antibody to a mammalian subject. In some embodiments, the method entails local administration of a composition comprising the antibody at or proximate to a tissue in the mammalian subject. In some embodiments, the tissue includes at least a cell that expresses CSF1R on the surface.

Also provided is a method for treating tenosynovial giant cell tumor (TGCT) in a patient, comprising administering an anti-CSF1R (colony stimulating factor 1 receptor) antibody at or proximate to the TGCT in the patient.

In some embodiments, the tissue is at a joint, which could be a knee, elbow, wrist, ankle or hip. In some embodiments, the local administration is intra-articular injection. In some embodiments, the joint is impacted with tenosynovial giant cell tumor (TGCT). In some embodiments, the local administration is intra-articular injection or intra-tumoral injection.

In some embodiments, the composition is administered at the tissue or tumor site. In some embodiments, the composition is administered proximate to the tissue or tumor site, such as equal to or less than 1 mm, equal to or less than 5 mm, equal to or less than 1 cm, equal to or less than 2 cm, or equal to or less than 5 cm from the tissue or tumor site.

In some embodiments, the anti-CSF1R antibody has an affinity to human CSF1R of Kd or IC50 that is lower than 1 nM, or lower than 0.9 nM, 0.8 nM, 0.7 nM, 0.6 nM, 0.5 nM, 0.4 nM, 0.3 nM, 0.2 nM, 0.1 nM, 0.05 nM, 0.01 nM, 0.005 nM or 0.001 nM. In some embodiments, the administration results in at least 2-fold, or 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, or 100-fold reduction of CSF1 activities at the tissue.

In some embodiments, the composition comprises at least 1 mg of the antibody. In some embodiments, the composition comprises at least 2, 3, 4, 5, 10, 20, 30, 40, 50, 60, 70, 80, 90, 100, 110, 120 130, 140, 150, 200, 300, 400, 500, 600, 700, 800, 900 or 1000 mg of the antibody. In some embodiments, the antibody concentration in the composition is at least 1 mg/mL, or at least 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, or 200 mg/mL.

In some embodiments, the administration results in a local (synovial) concentration of the anti-CSF1R antibody of at least 0.1 µg/mL two weeks following the administration. In some embodiments, the administration results in a local (synovial) concentration of the anti-CSF1R antibody of at least 0.2, or 0.3, 0.4, 0.5, 0.6, 0.7, 0.8, 0.9, 1.0, 1.5, 2, 2.5, 3, 4, 5, 6, 7, 8, 9, 10, 20, 30, 40, 50, 60, 70, 80, 90, 100, 150, 200, 250, 300, 350, 400, 450 or 500 µg/mL two weeks following the administration. In some embodiments, the administration results in a peak local (synovial) concentration of the anti-CSF1R antibody of at least 1.0, 1.5, 2, 2.5, 3, 4, 5, 6, 7, 8, 9, 10, 20, 30, 40, 50, 60, 70, 80, 90, 100, 150, 200, 250, 300, 350, 400, 450, 500, 600, 700, 800, 900, or 1000 µg/mL, or at least 1.0, 1.5, 2, 2.5, 3, 4, 5, 6, 7, 8, 9, 10, 20, 30, 40, or 50 mg/mL following the administration.

In some embodiments, the composition is an extended release composition. "Extended release," "controlled release", "sustained release", or "slow release" and similar terms are used to denote a mode of active agent delivery that occurs when the active agent is released from the delivery vehicle or depot over a period of time (at least 24 hours, 2 days, 3 days, 4 days, 5 days, 6 days, 1 week, 2 weeks, 3 weeks, 1 month, 2 months, 3 months, 4 months, 5 months or 6 months), rather than being dispersed immediately (e.g., at a diffusion-controlled rate) upon application or injection.

In some embodiments, the antibody is a human or humanized antibody. Example anti-CSF1R antibodies are provided in Table 1. Their sequences are provided in Table 2. In some embodiments, the antibody is Emactuzumab, Cabiralizumab, Axatilimab, IMC-CS4 or AM001. In some embodiments, the antibody is AM001, which includes a heavy chain comprising the sequence of SEQ ID NO:7 and a light chain comprising the sequence of SEQ ID NO:8. In some embodiments, the antibody is Emactuzumab, which includes a heavy chain comprising the sequence of SEQ ID NO:1 and a light chain comprising the sequence of SEQ ID NO:2.

TABLE 1

Example Anti-CSF1R Antibodies

| Name | Other Names | Type |
| --- | --- | --- |
| Emactuzumab | RG7155, or RO5509554 | IgG1 humanized |
| Cabiralizumab | FPA008 | IgG4 humanized |
| Axatilimab | SNDX-6352 | IgG4 humanized |
| IMC-CS4 | LY3022855 | IgG1 human |
| AM001 | | IgG2 human |

TABLE 2

Sequences of Example Anti-CSF1R Antibodies

| Antibody | Protein Sequences |
| --- | --- |
| Emactuzumab (RG7155, or RO5509554) | Heavy chain (SEQ ID NO: 1)<br>QVQLVQSGAEVKKPGASVKVSCKASGYTFTSYDISWVRQAPGQGLEWMGVIWTDGGTNYA<br>QKLQGRVTMTTDTSTSTAYMELRSLRSDDTAVYYCARDQRLYFDVWGQGTTVTVSSASTK<br>GPSVFPLAPSSKSTSGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKSRWQQGN<br>VFSCSVMHEALHNHYTQKSLSLSPGK<br><br>Light chain (SEQ ID NO: 2)<br>DIQMTQSPSSLSASVGDRVTITCRASEDVNTYVSWYQQKPGKAPKLLIYAASNRYTGVPS<br>RFSGSGSGTDFTLTISSLQPEDFATYYCQQSFSYPTFGQGTKLEIKRTVAAPSVFIFPPS<br>DEQLKSGTASVVCLLNNFYPREAKVQWKVDNALQSGNSQESVTEQDSKDSTYSLSSTLTL<br>SKADYEKHKVYACEVTHQGLSSPVTKSFNRGEC |
| Cabiralizumab (FPA008) | Heavy chain (SEQ ID NO: 3)<br>QVQLVQSGAEVKKPGSSVKVSCKASGYTFTDNYMIWVRQAPGQGLEWMGDINPYNGGTTF<br>NQKFKGRVTITADKSTSTAYMELSSLRSEDTAVYYCARESPYFSNLYVMDYWGQGTLVTV<br>SSASTKGPSVFPLAPCSRSTSESTAALGCLVKDYFPEPVTVSWNSGALTSGVHTFPAVLQ<br>SSGLYSLSSVVTVPSSSLGTKTYTCNVDHKPSNTKVDKRVESKYGPPCPPCPAPEFLGGP<br>SVFLFPPKPKDTLMISRTPEVTCVVVDVSQEDPEVQFNWYVDGVEVHNAKTKPREEQFNS<br>TYRVVSVLTVLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSRLTVDKSRWQ<br>EGNVFSCSVMHEALHNHYTQKSLSLSLGK<br><br>Light chain (SEQ ID NO: 4)<br>EIVLTQSPATLSLSPGERATLSCKASQSVDYDGDNYMNWYQQKPGQAPRLLIYAASNLES<br>GIPARFSGSGSGTDFTLTISSLEPEDFAVYYCHLSNEDLSTFGGGTKVEIKRTVAAPSVF<br>IFPPSDEQLKSGTASVVCLLNNFYPREAKVQWKVDNALQSGNSQESVTEQDSKDSTYSLS<br>STLTLSKADYEKHKVYACEVTHQGLSSPVTKSFNRGEC |
| IMC-CS4 (LY3022855) | Heavy chain (SEQ ID NO: 5)<br>QDQLVESGGGVVQPGRSLRLSCAASGFTFSSYGMHWVRQAPGEGLEWVAVIWYDGSNKYY<br>ADSVKGRFTISRDNSKNTLYLQMNSLRAEDTAVYYCARGDYEVDYGMDVWGQGTTVTVAS<br>ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKTHTCPPCPAPELLGG<br>PSVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDKSRW<br>QQGNVFSCSVMHEALHNHYTQKSLSLSPGK<br><br>Light chain (SEQ ID NO: 6)<br>AIQLTQSPSSLSASVGDRVTITCRASQGISNALAWYQQKPGKAPKLLIYDASSLESGVPS<br>RFSGSGSGTDFTLTISSLQPEDFATYYCQQFNSYPWTFGQGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| AM001 | Heavy chain (SEQ ID NO: 7)<br>QVQLVQSGAEVKKPGASVKVSCKASGYTFTSYGISWVRQAPGQGLEWMGWISAYNGNTNY<br>AQKLQGRVTMTTDTSTSTAYMELRSLRSDDTAVYYCARESWFGEVFFDYWGQGTLVTVSS<br>ASTKGPSVFPLAPCSRSTSESTAALGCLVKDYFPEPVTVSWNSGALTSGVHTFPAVLQSS<br>GLYSLSSVVTVPSSNFGTQTYTCNVDHKPSNTKVDKTVERKCCVECPPCPAPPVAGPSVF<br>LFPPKPKDTLMISRTPEVTCVVVDVSHEDPEVQFNWYVDGVEVHNAKTKPREEQFNSTFR<br>VVSVLTVVHQDWLNGKEYKCKVSNKGLPAPIEKTISKTGQPREPQVYTLPPSREEMTKN<br>QVSLTCLVKGFYPSDIAVEWESNGQPENNYKTTPPMLDSDGSFFLYSKLTVDKSRWQQGN<br>VFSCSVMHEALHNHYTQKSLSLSPGK |

TABLE 2-continued

Sequences of Example Anti-CSF1R Antibodies

| Antibody | Protein Sequences |
|---|---|
| | Light chain (SEQ ID NO: 8)<br>DIVMTQSPDSLAVSLGERATINCKSSQSVLDSSDNKNYLAWYQQKPGQPPKLLIYWASNR<br>ESGVPDRFSGSGSGTDFTLTISSLQAEDVAVYYCQQYYSDPFTFGPGTKVDIKRTVAAPS<br>VFIFPPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC |
| Axatilimab (SNDX-6352) | Heavy chain (SEQ ID NO: 9)<br>EVTLKESGPALVKPTQTLTLTCTFSGFSLTTYGMGVGWIRQPPGKALEWLANIWWDDDKY<br>YNPSLKNRLTISKDTSKNQVVLTMTNMDPVDTATYYCARIGPIKYPTAPYRYFDFWGQGT<br>MVTVSSASTKGPSVFPLAPCSRSTSESTAALGCLVKDYFPEPVTVSWNSGALTSGVHTFP<br>AVLQSSGLYSLSSVVTVPSSSLGTKTYTCNVDHKPSNTKVDKRVESKYGPPCPPCPAPEF<br>LGGPSVFLFPPKPKDTLMISRTPEVTCVVVDVSQEDPEVQFNWYVDGVEVHNAKTKPREE<br>QFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDK<br>SRWQEGNVFSCSVMHEALHNHYTQKSLSLSLGK<br><br>Light chain (SEQ ID NO: 10)<br>DIQMTQSPSSLSASVGDRVTITCLASEDIYDNLAWYQQKPGKAPKLLIYYASSLQDGVPS<br>RFSGSGSGTDYTLTISSLQPEDFATYYCLQDSEYPWTFGGGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |

Emactuzumab (also known as RG7155 and RO5509554) is a clinical stage humanized IgG1 CSF1R targeted antibody designed to target and deplete macrophages in the tumor tissue. It has shown a favorable safety profile in patients and encouraging efficacy for TGCT. Emactuzumab is under investigation in clinical trial NCT01494688—"A Study of RO5509554 as Monotherapy and in Combination with Paclitaxel in Participants With Advanced Solid Tumors."

Cabiralizumab (also known as FPA008) is under investigation in clinical trial NCT03502330—"APX005M With Nivolumab and Cabiralizumab in Advanced Melanoma, Non-small Cell Lung Cancer or Renal Cell Carcinoma." Cabiralizumab is a humanized IgG4 anti-CSF1R monoclonal antibody with a single amino acid substitution in the hinge region to prevent hemi-dimer exchange.

IMC-CS4 (also known as LY3022855) is a human IgG1 antibody (mAb) targeting CSF1R. IMC-CS4 is under investigation in clinical trial NCT01346358—"A Study of IMC-CS4 in Subjects With Advanced Solid Tumors."

AM001 is a fully human IgG2 anti-CSF1R antibody. Other example anti-CSF1R antibodies include PD-0360324 and GTX128677, without limitation.

Axatilimab (also known as SNDX-6352) is a humanized, full-length IgG4 antibody with high affinity to CSF-1R. Axatilimab affects the migration, proliferation, differentiation, and survival of monocytes and macrophages by binding to CSF-1R and blocking its activation by its two known ligands, CSF-1 and IL-34. Axatilimab is currently being evaluated in a Phase 1/2 clinical trial in patients with cGVHD.

The composition to be administered, in some embodiments, includes a minimum concentration of the antibody. In some embodiments, the minimum concentration is 2 mg/mL, or 5 mg/mL, 10 mg/mL, 15 mg/mL, 20 mg/mL, 25 mg/mL, 30 mg/mL, 40 mg/mL, 50 mg/mL, 75 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or 250 mg/mL.

In some embodiments, the composition to be administered is adjusted to have a suitable pH. In one embodiment, the pH is 4 to 10, 4 to 9.5, 4 to 9, 4 to 8.5, 4 to 8, 4 to 7.5, 4 to 7, 4 to 6.5, 4 to 6, 4 to 5.5, 4 to 5, 4.5 to 10, 4.5 to 9.5, 4.5 to 9, 4.5 to 8.5, 4.5 to 8, 4.5 to 7.5, 4.5 to 7, 4.5 to 6.5, 4.5 to 6, 4.5 to 5.5, 4.5 to 5, 4.9 to 10, 4.9 to 9.5, 4.9 to 9, 4.9 to 8.5, 4.9 to 8, 4.9 to 7.5, 4.9 to 7, 4.9 to 6.5, 4.9 to 6, 4.9 to 5.5, 5.5 to 10, 5.5 to 9.5, 5.5 to 9, 5.5 to 8.5, 5.5 to 8, 5.5 to 7.5, 5.5 to 7, 5.5 to 6.5, 5.5 to 6, 6 to 10, 6 to 9.5, 6 to 9, 6 to 8.5, 6 to 8, 6 to 7.5, 6 to 7, 6 to 6.5, 6.5 to 10, 6.5 to 9.5, 6.5 to 9, 6.5 to 8.5, 6.5 to 8, 6.5 to 7.5, 6.5 to 7, 7 to 10, 7 to 9.5, 7 to 9, 7 to 8.5, 7 to 8, 7 to 7.5, 7.5 to 10, 7.5 to 9.5, 7.5 to 9, 7.5 to 8.5, 7.5 to 8, 8 to 10, 8 to 9.5, 8 to 9, 8 to 8.5, 8.5 to 10, 8.5 to 9.5, 8.5 to 9, 9 to 10, 9 to 9.5, or 9.5 to 10. In one embodiment, the pH is 4.9 to 5.5.

In some embodiments, the composition further includes other ingredients as disclosed below, which forms an extended release formulation.

In some embodiments, the composition is administered at the tumor site. In some embodiments, the composition is administered proximate to the tumor site, such as equal to or less than 1 mm, equal to or less than 5 mm, equal to or less than 1 cm, equal to or less than 2 cm, or equal to or less than 5 cm from the tumor site. In a preferred embodiment, the pharmaceutical composition is administered by intra-articular injection into the impacted joint. In some embodiments, the pharmaceutical composition is administered by subcutaneous or intramuscular injection.

In some embodiments, the methods are for treating a patient having TGCT or other tumors (e.g., melanoma, glioblastoma, leukemia, and congenital hypertrichosis lanuginosa (CHL)) that can be suitably treated with CSF1R inhibition.

III. Antibody Formulations

Formulations containing the antibodies of the present disclosure are also provided.

In some embodiments, provided is a pharmaceutical composition for local administration, providing controlled release of the therapeutic agent in the pharmaceutical composition. The controlled release excipient may be a gel-forming excipient, in particular, when the therapeutic agent is a large molecule such as an antibody. Preferred gel-forming excipients are thermogels. The controlled release excipient may be a biodegradable matrix. Preferably, a biodegradable matrix is formulated as microspheres for delivery of small molecule therapeutic agent. The composition may be formulated for injection. The therapeutic agent, in some embodiments, is an antibody of the present disclosure.

Controlled release may provide sustained release of a therapeutic agent, extending for hours, days or months, or may provide pulsatile release of the therapeutic agent, and may vary as a function of numerous factors. The rate of release may depend on factors including the type and the concentration of the therapeutic agent and the excipient in the composition and location of administration.

In some embodiments, the composition comprises about 1% w/w to about 90% w/w, or about 5% w/w to about 80% w/w, or about 10% w/w to about 70% w/w of the antibody based on the total weight of the composition. In some embodiments, the composition comprises about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% w/w of the antibody based on the total weight of the composition, or within any range between any two of the values, end points inclusive.

In some embodiments, the antibody is released from the composition in a controlled manner (e.g., releasing a daily therapeutic amount each day) over a period of time, such as 1 day, 2 days, 1 week, 2 weeks, 3 weeks, 6 weeks, 1 month, 2 months, 3 months or 6 months. In some embodiments, each administration results in sustained exposure of the antibody for at least 3 weeks, 4 weeks, 2 months, 3 months, 4 months, or 6 months. In some embodiments, the effective amount is for local administration and is less than that needed for systemic administration, such as, equal to or less than 90%, equal to or less than 80%, equal to or less than 70%, equal to or less than 60%, equal to or less than 50%, equal to or less than 40%, equal to or less than 30%, equal to or less than 20%, equal to or less than 10%, equal to or less than 5%, or equal to or less than 1%, of a corresponding effective amount for systemic administration, or any range between any of the two numbers, endpoints inclusive.

In some embodiments, the composition is a controlled release formulation that releases the antibody to provide a therapeutically effective amount over an extended period of time. In some embodiments, the composition releases a therapeutically effective amount of antibody inhibitor for 1 week, 2 weeks, 3 weeks, 1 month, 2 months, 3 months, or 6 months. In preferred embodiments, the controlled release formulations provide therapeutically effective amounts of the antibody when administered once or twice monthly.

In some embodiments, the composition is a controlled release formulation that contains a mixture of microparticles designed to release the antibody at different times. For example, the composition may release the antibody in a pulsatile mode where different populations of microparticles are designed to release therapeutic doses as discrete bursts over a prespecified time.

In some embodiments, the gel-forming excipient is a thermogel having a transition temperature of above room temperature but below or at body temperature. In this embodiment, the formulation is an injectable liquid at room temperature that converts to a gel phase after administration. In some embodiments, the composition has a transition temperature of about 25° C. to about 36° C. or about 28° C. to about 35° C. Upon conversion to a gel phase after administration, the therapeutic agent is released slowly from the gel, allowing therapeutic effect. In some embodiments, the thermogel is biodegradable.

A gel-forming excipient may provide sustained release of the therapeutic agent by forming a gel upon administration, such as is the case with thermogels, or by enhancing the viscosity of the formulation. Gel-forming excipients include polymers selected from poloxamer, hyaluronic acid (HA), alginate, hydroxy methylcellulose (HPMC), hydroxy propylcellulose (HPC), sodium carboxymethylcellulsoe (NaCMC) or polyvinyl povidone (PVP). In some embodiment the composition comprises a viscosity enhancing agent such as NaCMC, hydroxypropyl cellulose (HPC), or polyvinyl pyrrolidone (PVP).

In some embodiments the polymer encapsulates the active ingredient in microspheres or nanospheres and comprises a biodegradable material such as poly(D,L-lactic acid) (PLA), poly(D,L-lactic-co-glycolic acid) (PLGA), or a block copolymer comprising hydrophilic poly(ethylene glycol) (PEG) and one or more polymers selected from poly(lactic acid-co-glycolic acid) (PLGA), poly(ε-caprolactone) (PCL), and poly(ε-caprolactone-co-glycolic acid) (PCGA), such as poly (ε-caprolactone-co-glycolic acid)-poly(ethylene glycol)-poly(ε-caprolactone-co-glycolic acid) (PCGA-PEG-PCGA) and poly(lactic acid-co-glycolic acid)-poly(ethylene glycol)-poly(lactic acid-co-glycolic acid) (PLGA-PEG-PLGA), or a combination thereof. Long-chain or medium chain triglycerides may be incorporated into the microshperes or nanosperes to further enhance stability and/or drug release from the microspheres or nanospheres. See, e.g., Meng, B, et al., Int'l J. Pharm., Vol 397 (1-2), 136-142 (2010).

In some embodiments, the composition comprises about 5% to about 50% of the gel-forming excipient based on the total weight of the composition. In some embodiments, the composition comprises about 5%, 10%, 15%, 20%, 25%, 30%, 35%, 40%, 45% or 50% of the gel-forming excipient based on the total weight of the composition, or any range between any two of the values, endpoints inclusive.

In some embodiments, the thermogel comprises hyaluronic acid (HA) or a pharmaceutically acceptable salt thereof. Hyaluronic acid is a mucopolysaccharide consisting of N-acetylglucosamine and glucuronic acid. The pharmaceutically acceptable salts of HA include the salts with lithium, sodium, potassium, magnesium, calcium and the like. In some embodiments, HA or its pharmaceutically acceptable salt has a molecular weight of about $2 \times 10^5$ to $5 \times 10^6$ Daltons, or about $5 \times 10^5$ to $3 \times 10^6$ Daltons, or about $7 \times 10^5$ to $2.5 \times 10^6$ Daltons. In some embodiments, the composition comprises about 5%, 10%, 15%, 20%, 25%, 30%, 35%, 40%, 45% or 50% HA.

In some embodiments, the thermogel comprises a poloxamer. Poloxamers are biocompatible polyoxyethylene-polyoxypropylene block copolymers that are also known by their tradenames such as Pluronics® and Lutrol®. There are several types of poloxamers based on the molecular weight and the amount of oxyethylene and oxypropylene units, for example, poloxamers 124, 182, 188, 237, 338 and 407. When dissolved in water or an aqueous solvent, they form a thermogel.

In some embodiments, the thermogel comprises about 25% to 33% of poloxamer 407 or poloxamer 188, or a combination thereof, and an aqueous solvent, such as water or an aqueous buffer. In some embodiments, the thermogel comprises about 25% to 33% of a mixture of poloxamer 407 or poloxamer 188 in a ratio of between 3:1 and 0.8:1.

In some embodiments, the composition comprises a biodegradable matrix. The biodegradable matrix comprises a biodegradable polymer. Examples of biodegradable polymers include, but are not limited to, polycyanoacrylates, polyurethanes, polyorthoester, polyacetals, polyesters, such as poly(D,L-lactic acid) (PLA) and poly(D,L-lactic-co-glycolic acid) (PLGA), poly hydroxyl butyrate, polyester, polycaprolactone, poly lactide-co-glycolide (PLGA), and poly diaxonone; polyanhydride, such as poly adepic acid, poly sebacic acid, and poly terpthalic acid; polyamides, such as poly amino acid, and poly imino carbonate; phosphorous based polymer, such as polyphosphates, poly phosphonates, and poly phosphazenes. Other examples of biodegradable polymers include poly(ricinoleic acid) (RA); poly(fumaric acid) (FA); poly(fatty acid dimer) (FAD); poly(terephthalic acid) (TA); poly(isophthalic acid) (IPA); poly(p-{carboxyphenoxy}methane) (CPM); poly-{carboxyphenoxy}propane) (CPP); poly(p-{carboxyphenoxy}hexane) (CPH); polyamines, polyesteramides, (CHDM: Cis/trans-cyclohexyl dimethanol, HD:1,6-hexanediol (3,9-diethylidene-2,4,8,10-tetraoxaspiro undecane) (DETOSU); polydioxanones; polyhydroxybutyrates; polyalkyene oxalates; polyketals; polycarbonates; polyorthocarbonates; polysiloxanes; succinates; hyaluronic acid; poly(malic acid); polyhydroxyvalerates; polyalkylene succinates; polyvinylpyrrolidone; polyacrylic acids; polybutyric acid: polyvaleric acid; and poly(glutamic acid-co-ethyl glutamate), copolymers and/or mixtures thereof. In some embodiments, the biodegradable matrix comprises PLA and/or PLGA microspheres.

Certain polymers are both biodegradable and can form a thermogel, for example, block copolymers of polyethylene oxide and poly(L-lactic acid).

In some embodiments, the therapeutic agent is formulated as a complex with a complexing agent such as a cyclodextrins or a resin, then formulated as microspheres. In this embodiment, the therapeutic agent is preferable a small molecule. The complexing agent prolongs release of the therapeutic agent. Formulations in which the therapeutic agent is formulated as microspheres with a complexing agent may optionally include a viscosity enhancing agent. In some embodiments, the cyclodextrin is hydroxypropyl-β-cyclodextrin or sulfobutyl ether-β-cyclodextrin.

As used herein, "microparticles" refers to particles having a diameter of less than 1 mm, more or less than 900 µm, 800 µm, 700 µm, 600 µm, 500 µm, 400 µm, 300 µm, 200 or 100 µm. Microparticles can be "microspheres", which are solid spherical microparticles, and microcapsules, which are spherical microparticles having a core of a different polymer, drug, or composition.

Many polymers can be used to prepare the microspheres for controlled drug delivery. Polymers typically are thermoplastic synthetic polymers, such as ethylene vinyl acetate and poly(acrylic acid), which are generally viewed as non-biodegradable since they remain in relatively the same form over a period of at least two or three years following implantation in the body, and biodegradable polymers, such as poly(hydroxy acids) including polylactic acid, polyglycolic acid, and copolymers thereof, polyanhydrides, polyorthoesters, and certain types of protein and polysaccharide polymers. A polymer may have a half life in the biological environment of about 1 week to about 10 years, for example, about 1 week, about 1 month, about 6 months, about 1 year, about 5 years, about 10 years, or a range of values between any two of these.

An example polymer material is one which is biodegradable and which retains sufficient form to control release for a period following implantation of at least six to seven days. The poly (hydroxy acids), especially poly(lactic acid-co-glycolic acid) ("PLGA"), is a particularly useful polymer and has been used in the manufacture of degradable sutures for several decades. The polymer degrades by hydrolysis following exposure to the aqueous environment of the body. The polymer is hydrolyzed to yield lactic and glycolic acid monomers, which are normal byproducts of cellular metabolism. The rate of polymer disintegration can vary from several weeks to periods of greater than one year, depending on several factors including polymer molecular weight, ratio of lactide to glycolide monomers in the polymer chain, and stereoregularity of the monomer subunits (mixtures of L and D stereoisomers disrupt the polymer crystallinity enhancing polymer breakdown).

Particularly useful results can be obtained by blending PLGA having different molecular weights, and/or different ratios of lactide to glycolide. The molecular weight and monomer ratios can be optimized to tailor the release kinetics over a defined period of time. The higher molecular weights result in polymer matrices which retain their structural integrity for longer periods of time; while lower molecular weights, result in both faster release and shorter matrix lives.

In some embodiments, the microspheres contain blends of at least two and more preferably three or more biodegradable polymers, preferably hydrolytically unstable polymers, most preferably poly(hydroxy acids) of different molecular weight and/or monomer ratio. In a preferred embodiment, three different molecular weight PLGAs are blended to form a composition that has linear release over a defined period of time, ranging from at least one day to about sixty days. In a more preferred embodiment to obtain release from about one to twenty-one days, the PLGAs have molecular weights between 1000 and 20,000, more preferably between 5,000 and 10,000, between 20,000 and 35,000, more preferably between 25,000 and 30,000, and between 35,000 and 70,000, more preferably 5000 and 10,000. In the most preferred embodiment for release over a period of about one week, PLGAs having molecular weights of about 6,000, 30,000, and 41,000 are combined. In some embodiments, the microspheres may contain medium or long-chain triglycerides to enhance stability and/or drug release.

PLA polymers can be prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature.

Microsphere formulations may be prepared with combinations of different populations of microspheres as described herein. Each population of microspheres in the combination may be designed to release the therapeutic agent at different rates, thereby providing prolonged therapeutic effect. In some embodiments, the formulation provides a pulsatile release of the therapeutic agent by combining populations of micro spheres, wherein each population is designed to release the therapeutic agent in a single burst at prespecified periods of time.

In some embodiment the release retarding agent is a high molecular weight polymer that is covalently bound to the therapeutic agent to prolong the circulating half-life. For example, the therapeutic agent may be PEGylated with high molecular weight PEG. PEGylation is a preferred embodiment where the therapeutic agent is a large molecule such as an antibody.

In some embodiments, the therapeutic agent is administered locally via implantation of a depot drug delivery vehicle. Implantation will be at, inside the tumor or near the tumor site and may occur in connection with surgery to remove tumor mass. Depot drug delivery systems have been developed for implantation, providing localized drug delivery over an extended period of time. Such drug delivery systems can take several forms, including gels, films, wafers, rods and particles and are designed to provide predictable controlled release of the therapeutic agent. See Wolinski, J B, Colson, Y L, and Grinstaf, M W, J Control Release, 2012 Apr. 10: 159(1). Preferred implantable delivery systems are biodegradable polymers.

The polymers used in implantable delivery systems may be natural or synthetic. Natural polymeric systems include polysaccharides such as alginate, hyaluronic acid, dextran and chitosan, and polypeptides such as collagen, albumin, elastin and gelatin. Such polymeric delivery systems may form gels upon administration, and thereby provide prolonged local drug delivery. Synthetic polymers for drug depot implants are known and include polyesters based on lactide, glycolide, caprolactone, and dioxanone, polyanhydrides based on sebacic and adipic acid, and polyamides, polycarbonates, polyorthoesters and phosphate-based polymers. Synthetic polymeric systems are often hydrophobic and are well-suited to prolonged delivery of water-insoluble drugs.

In some embodiments, the formulation includes one or more tonicity agents. The term "tonicity agent" as used herein denotes pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, or suspension that solubilize up on dilution, e.g. from a lyophilized form and denotes a solution having the same tonicity as some other solution with which it is compared, such as physiologic salt solution and the blood serum. Suitable isotonicity agents include but are not limited to sodium chloride, potassium chloride, glycerin and any component from the group of amino acids, sugars, as defined herein as well as combinations thereof.

In some embodiments, the formulation includes one or more surfactants. As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical formulations and preparations of biological materials. In some embodiments of the pharmaceutical formulations described herein, the amount of surfactant is described as a percentage expressed in weight/volume percent (w/v %). Suitable pharmaceutically acceptable surfactants include but are not limited to the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween 20™) and polysorbate 80 (sold under the trademark Tween 80™). Polyethylene-polypropylene copolymers include those sold under the names Pluronic® F68 or Poloxamer 188™. Polyoxyethylene alkyl ethers include those sold under the trademark Brij™. Alkylphenolpolyoxyethylene ethers include those sold under the tradename Triton-X.

In some embodiments, the formulation further includes one or more antioxidants. An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the protein therapeutics and ultimately affect the product activity. Antioxidants terminate these chain reactions by removing free radical intermediates and inhibit other oxidation reactions by being oxidized themselves. As a result, antioxidants are often reducing agents, chelating agent and oxygen scavengers such as citrate, EDTA, DPTA, thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

In some embodiments, the formulation further includes one or more preservatives. A "preservative" is a natural or synthetic chemical that is added to products such as foods, pharmaceuticals, paints, biological samples, wood, etc. to prevent deformulation by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA. Other preservatives include those commonly used in patenteral proteins such as benzyl alcohol, phenol, m-cresol, chlorobutanol or methylparaben.

In some embodiment the formulation further includes buffering system such as citrate, acetate, borate, phosphate or combination of. In some embodiment the formulation further includes tertiary butanol to enhance property and stability of lyophilized material.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Example 1. Efficacy and Extended Exposure of Intra-Articularly Administered AM001

This experiment tested the pharmacokinetics, pharmacodynamics, and efficacy of AM001 in treating TGCT through intra-articular injection to the joint.

Eight patients having diffuse-type TGCT in the knees were recruited in the trial. Each patient received one shot every two weeks of the anti-CSF1R antibody AM001 (150 mg), via intra-articular injection into the impacted joint. At the 6-week interval and at the end of the 12-week period and 12 weeks later, the tumor mass was measured with MRI.

Objective Responses (OR, >30% tumor reduction) was measured in TGCT lesions for the long dimension (RECIST1.1) and the short lesion dimension (Modified RECIST).

Three of eight of the patients demonstrated Objective Responses by RECIST1.1 and 4 of 8 showed ORs by Modified RECIST by the end of the study and the majority of these tumor reduction responses were evident at the Week 6 MRI. Moreover, all patients exhibited meaningful improvements in range of motion and reduced pain.

In terms of exposure, the average synovial vs serum AM001 level in the three patients at 2 weeks after the first 150 mg dose: mean 17,237 ng/ml synovial vs 5,962 ng/ml serum. With the pharmacodynamic measure of CSF1 levels, increases were over 100-fold on average—6,184 pg/ml synovial and 1,071 pg/ml serum, p<0.05. AM001 synovial concentrations showed marked accumulation during the trial further validating long-term residence and low clearance in the joint. And the ratio of synovial to serum levels was >5-fold by the end of the treatment period. This example, therefore, demonstrated that intra-articular administration of AM001 resulted in high and extended synovial AM001 concentrations with consistently reduced and low systemic exposure, pharmacologic activity commensurate with pharmacokinetics, and clinically significant and meaningful treatment effects.

Three patients received a 90 mg dose bi-weekly and pharmacokinetic, pharmacodynamic, and tumor reduction responses were similar (and dose-proportional) to the 150 mg cohort.

Example 2. Nonclinical Testing of AM001

This example conducted nonclinical testing for AM001.
Pharmacokinetics of Intravenous AM001

Single IV doses of AM001 administered to cynomolgus monkeys produced a nonlinear increase in exposure at doses of 0.1 to 5 mg/kg but an approximately dose-proportional increase at doses of 5 to 100 mg/kg. When receptor-mediated clearance had been saturated at higher serum concentrations of AM001 (>100 μg/mL), the kinetics of AM001 became linear. The volume of distribution at steady state for AM001 in monkeys was approximately equal to plasma volume, indicating limited extravascular distribution.

The toxicokinetics of repeated IV doses of AM001 was assessed in both 4-week and 14-week repeat-dose Good Laboratory Practice (GLP) toxicity studies in cynomolgus monkeys and did not differ markedly between male and female monkeys. In general, exposure to IV AM001 increased approximately dose proportionally in monkeys over the dose range of 10 to 300 mg/kg. No marked (>2-fold) accumulation of AM001 was observed after either 4 or 13 once-weekly doses in monkeys. During the dosing phase of these studies, AM001-binding ADAs (anti-drug antibodies) were detected in 1 of 30 animals in the 4-week study and 13 of 35 animals in the 14-week study; during the recovery phase of the 14-week study, ADAs were detected in 8 of 10 animals. In general, ADAs decreased exposure to AM001 in these animals. For both studies, high concentrations of AM001 in the serum samples may have interfered with detection of ADAs in animals that tested ADA-negative.

Synovial concentrations of AM001 can be extrapolated from the 14-week cynomolgus monkey studies. In these studies, peak serum concentrations over the dosing period were ~5 mg/mL, which translates to synovial concentrations of ≥50 μg/mL at steady-state.

Pharmacokinetics of Intra-Articular AM001

A small set of non-GLP investigations assessed IA injection of AM001 at various doses (1.5, 2.5, and 5 mg/kg) into the synovium of the knee of healthy, naïve, male cynomolgus monkeys. The first investigation tested sequential injection of a dose of 1.5 mg/kg (equivalent to a human dose of ~100 mg) into 1 knee each of 4 animals, followed 3 weeks later by a second dose of ~2.5 mg/kg (equivalent to a human dose of ~160 mg) into the other knee. A subsequent investigation tested a single IA injection of 5 mg/kg (equivalent to a human dose of ~330 mg), again into 1 knee each of 4 animals. Serum and synovial fluid AM001 levels were followed over time, and local and systemic tolerability were monitored.

AM001 was clearly evident in both serum and synovial fluid and exhibited similar elimination kinetics in both compartments, though systemic drug levels were typically approximately ¼ to ⅕ of synovial drug levels. AM001 drug levels were generally consistent with modeled projections and were approximately dose proportional. At the 1.5 mg/kg dose, the mean±standard deviation (SD) serum AM001 $C_{max}$ was 9.4±2.6 μg/mL and declined to 0.05±0.06 μg/mL over the week following dosing. Following the 2.5 mg/kg dose, serum and synovial drug levels increased approximately linearly from the 1.5 mg/kg dose in 2 of 4 animals but were very low in the other 2 animals, likely because of ADA. Of the 4 animals administered the 5 mg/kg dose, 2 to possibly 3 animals exhibited ADA activity by Day 28. Serum area under the curve $(AUC)_{last}$ values averaged 863 μg·hr/mL at 1.5 mg/kg, 1,248 μg·hr/mL at 2.5 mg/kg (for the 2 animals with substantial exposures), and 2,928 μg·hr/mL at 5 mg/kg. These values are well below that associated with AEs of note in the Phase ½ clinical trial in subjects with select advanced solid tumors. Following the 5 mg/kg dose, synovial AM001 levels in the injected knee remained at predicted efficacious levels for the entire 28-day duration of the investigation.

Toxicology

In GLP toxicology studies in the cynomolgus monkey, animals received IV AM001 at up to 300 mg/kg once-weekly for 4 or 14 weeks. All directly AM001-related findings were attributed to its expected pharmacology of inhibition of macrophages. Additionally, changes related to the acute post-dosing formation of ADA/drug complex occurred in some animals in the 14-week study.

Clinical observations attributed to AM001 pharmacology consisted of reversible periorbital swelling due to increased extracellular matrix, as observed by light microscopy. Clinical pathology changes included reversible increases in serum ALT, AST, and glutamate dehydrogenase (GLDH) without a light microscopic correlate in the liver and without elevations in sorbitol dehydrogenase (SDH), a liver-specific marker of injury. The increased extracellular matrix and elevated activities of hepatic transaminases were thought to result from decreased clearance due to inhibition of macrophages. Additional AM001-related changes included decreased bone turnover, characterized by elongation of bone growth plates, decreased numbers of osteoclasts, and decreases in serum markers of bone turnover, all of which were reversible and related to CSF1R-targeted pharmacology.

In the non-GLP investigations of IA AM001 1.5 to 5 mg/kg in cynomolgus monkeys, there were no AM001-related adverse observations, including for knee range of motion or general mobility.

Example 3. Clinical Testing of Intra-Articular Injection of AM001

This human trial evaluated the safety, efficacy, and PK of Intraarticular (IA) injection of AM001 in the treatment of TGCT.

Enrolled patients were at least 18 years old, with confirmed TGCT of knee (actual ages: 20-74; median: 32; 5 females and 6 males). It was a 12-week treatment with IA injections of AM001, bi-weekly. Eight patients received 150 mg of AM001 per dose, and 3 patients received 90 mg of AM001 per dose. Key outcomes measured included objective response rate (ORR) per MRI, improvements in pain, stiffness, range-of-motion, quality-of-life, PK, PD and safety.

The IA administration of AM001 yielded high, sustained synovial concentrations, while its serum levels were with markedly reduced, in both cohorts (FIG. 1).

Figure 2:
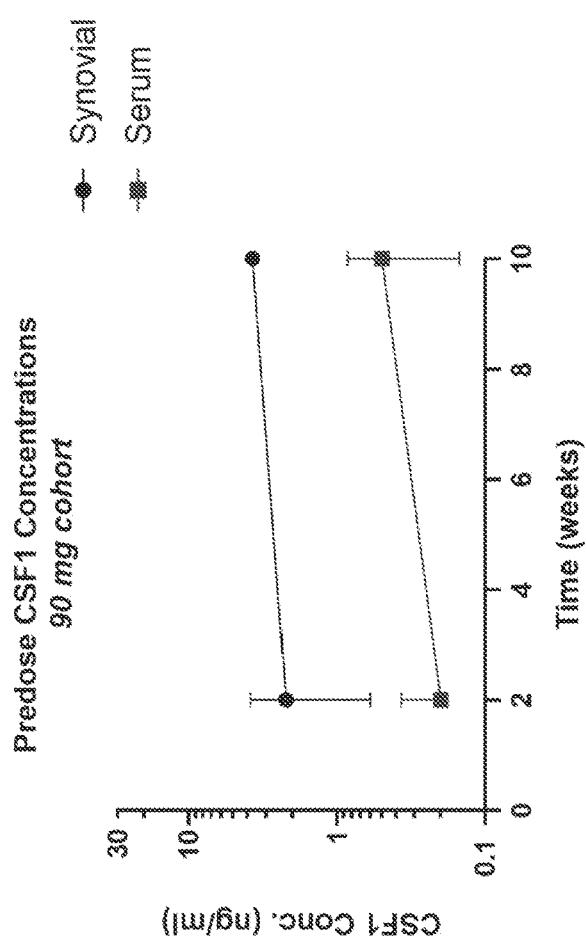
FIG. 2 shows that the pharmacologic activity of AM001 was evident early and was locally concentrated.
Figure 2:
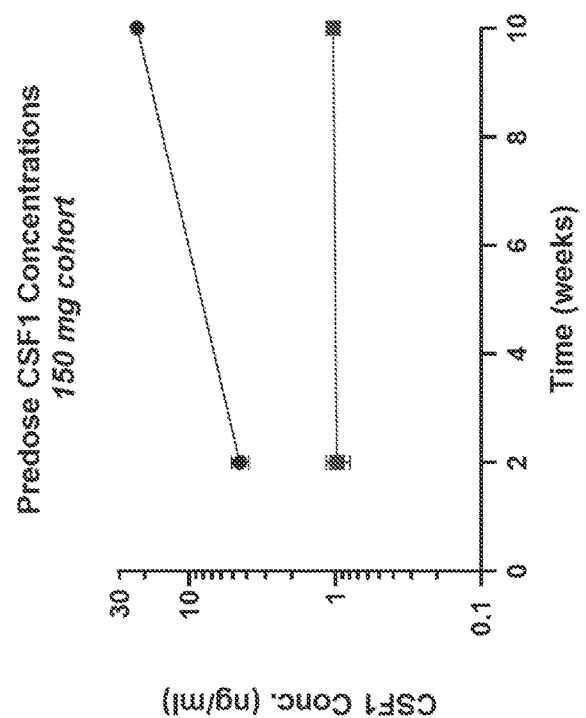

The pharmacologic activity of AM001, as measured by changes of CSF1 concentrations, was evident early and was locally concentrated. This is demonstrated in FIG. 2. For reference, baseline CSF concentrations were ~30 pg/ml in the synovium and were ~10 pg/ml in the serum.

The clinical efficacy responses at weeks 6, 12, and 24 were measured and best overall responses are presented in Table 1A (150 mg cohort) and Table 1B (90 mg cohort). There were clear benefits across multiple clinically-relevant endpoints, which demonstrate the overall robustness of efficacy signal with AM001.

TABLE 1A

Clinical Efficacy Response at Week 12 (150 mg, N = 8)

| Clinical Endpoint | Baseline Result | Week 12 Result | Improved? |
|---|---|---|---|
| Pain | | | |
| Overall Severity | 3.6 | 1.2 | YES |
| Overall Pain Interference | 3.8 | 1.0 | YES |
| Worst Pain | 5.1 | 2.3 | YES |
| Average Pain | 3.8 | 1.5 | YES |
| Stiffness | 5.0 | 2.0 | YES |
| ROM (Flexion) | 108° | 128° | YES |
| Quality of Life | | | |
| PROMIS | 36.3 | 43.0 | YES |
| EQ-5D-5L | 11.0 | 7.6 | YES |

TABLE 1B

Clinical Efficacy Response at Week 12 (90 mg, N = 3)

| Clinical Endpoint | Baseline Result | Week 12 Result | Improved? |
|---|---|---|---|
| Pain | | | |
| Overall Severity | 4.7 | 2.1 | YES |
| Overall Pain Interference | 4.4 | 1.9 | YES |
| Worst Pain | 6.7 | 3.7 | YES |

TABLE 1B-continued

Clinical Efficacy Response at Week 12 (90 mg, N = 3)

| Clinical Endpoint | Baseline Result | Week 12 Result | Improved? |
|---|---|---|---|
| Average Pain | 5.0 | 2.0 | YES |
| Stiffness | 5.7 | 3.3 | YES |
| ROM (Flexion) | 120° | 130° | YES |
| Quality of Life | | | |
| PROMIS | 35.0 | 43.7 | YES |
| EQ-5D-5L | 11.3 | 8.3 | YES |

\* Higher scores are better on the PROMIS. Lower scores are better on Pain (including all sub-scores), Stiffness, and the EQ-5D-5L. Pain and Stiffness scored on a scale from 0-10; PROMIS ranges from 0-50; EQ-5D-5L ranges from 0-25.

Table 2 lists the best overall tumor responses based on independent central radiology review (tumor reduction observed via MRI across all patients per 2 blinded reviewers).

TABLE 2

Best Overall Tumor Response

| Cohort (N) | Objective Response Rate (ORR) per | ORR (n = 11) |
|---|---|---|
| 150 mg (N = 8) | Standard RECIST v1.1\* | 3/8 (38%) |
| | Modified RECIST\*\* | 4/8 (50%) |
| 90 mg (N = 3) | Standard RECIST v1.1\* | 1/3 (33%) |
| | Modified RECIST\*\* | 1/3 (33%) |

\*Threshold for RECIST v.1.1: ≥30% reduction in sum of long-axis of lesions
\*\*Threshold for modified RECIST: ≥30% reduction in sum of short-axis of lesions An important observation from this trial is that the residence of AM001 in the synovial fluid was better than expected. The accumulation over the Q2Wk dosing treatment period was ~5-fold (at 150 mg and >5-fold in the 90 mg cohort). Hence, the residence in the joint was >2-weeks and much longer than researchers had proposed. Meanwhile, systemic AM001 concentrations are ≤1/5 synovial levels at most time points.

The pharmacodynamic marker, CSF1, was increased promptly in both synovial and serum compartments and achieved a plateau within 4-6 weeks. CSF1 levels in synovial fluid were ~20-fold> in serum.

The results therefore shows that IA administration of AM001 yielded high local drug levels and pharmacologic activity with minimal systemic exposures and AE risk.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A method for administering an anti-CSF1R (colony stimulating factor 1 receptor) antibody to a mammalian subject, comprising local administration of a composition comprising the antibody at or proximate to a tissue in the mammalian subject, wherein the tissue is a joint impacted with tenosynovial giant cell tumor (TGCT), and wherein the tissue comprises at least a cell that expresses CSF1R on the surface.

2. The method of claim 1, wherein the antibody is selected from the group consisting of AM001, Emactuzumab, Cabiralizumab, Axatilimab and IMC-CS4.

3. The method of claim 1, wherein the composition comprises at least 10 mg of the antibody.

4. The method of claim 3, wherein the composition comprises at least 50 mg of the antibody.

5. The method of claim 1, wherein the joint is a knee, elbow, wrist, ankle or hip.

6. The method of claim 1, wherein the administration is intraarticular injection.

7. The method of claim 1, wherein the local administration is intra-articular injection or intra-tumoral injection.

8. The method of claim 1, wherein the composition further comprises a polymer selected from the group consisting of hyaluronic acid (HA), a poloxamer, alginate, hydroxy methylcellulose (HPMC), hydroxy propylcellulose (HPC), poly (D,L-lactic acid) (PLA), poly(D,L-lactic-co-glycolic acid) (PLGA), a block copolymer comprising hydrophilic poly (ethylene glycol) (PEG) and one or more polymers selected from poly(lactic acid-co-glycolic acid) (PLGA), poly(ε-caprolactone) (PCL), and poly(ε-caprolactone-co-glycolic acid) (PCGA), and combinations thereof.

9. The method of claim 1, wherein the administration results in sustained exposure of the antibody for at least 3 weeks, 4 weeks, 2 months, 3 months, 4 months, or 6 months.

10. The method of claim 1, wherein the administration is once every 2 weeks, 3 weeks, 4 weeks, 2 months, 3 months, 4 months, 6 months, or longer.

11. A method for treating tenosynovial giant cell tumor (TGCT) at a joint in a patient, comprising administering an anti-CSF1R (colony stimulating factor 1 receptor) antibody at or proximate to the TGCT at the joint in the patient.

12. The method of claim 11, wherein the TGCT expresses CSF1R on cell surfaces.

13. The method of claim 11, wherein the administering is via intra-articular or intra-tumoral injection.

14. The method of claim 11, wherein the antibody is selected from the group consisting of AM001, Emactuzumab, Cabiralizumab, Axatilimab and IMC-CS4.

15. The method of claim 11, wherein the administration results in sustained exposure of the antibody for at least 3 weeks, 4 weeks, 2 months, 3 months, 4 months, or 6 months.

16. The method of claim 11, wherein the administration is once every 2 weeks, 3 weeks, 4 weeks, 2 months, 3 months, 4 months, 6 months, or longer.

17. The method of claim 1, wherein the antibody is AM001.

18. The method of claim 11, wherein the antibody is AM001.

* * * * *